US006612153B2

(12) United States Patent
White et al.

(10) Patent No.: US 6,612,153 B2
(45) Date of Patent: Sep. 2, 2003

(54) PLANAR MANIFOLD WITH INTEGRATED HEATED INJECTOR INLET AND UNHEATED PNEUMATICS

(75) Inventors: Richard P. White, Glen Mills, PA (US); Alan D. Loux, Newark, DE (US)

(73) Assignee: Agilent Technologies, Inc., Palo Alto, CA (US)

(*) Notice: Subject to any disclaimer, the term of this patent is extended or adjusted under 35 U.S.C. 154(b) by 35 days.

(21) Appl. No.: 09/873,391

(22) Filed: Jun. 5, 2001

(65) Prior Publication Data

US 2002/0178786 A1 Dec. 5, 2002

(51) Int. Cl.[7] .............................. G01N 30/04; F16K 1/00
(52) U.S. Cl. ..................... 73/23.42; 73/863.72; 137/884
(58) Field of Search ........................ 73/23.42, 863.71, 73/863.72; 137/884; 96/105, 106; 95/87

(56) References Cited

U.S. PATENT DOCUMENTS

| | | | | |
|---|---|---|---|---|
| 3,213,883 A | * | 10/1965 | Carls ........................ 137/884 |
| 5,601,785 A | * | 2/1997 | Higdon ..................... 210/198.2 |
| 5,686,657 A | | 11/1997 | Craig et al. |
| 5,767,387 A | * | 6/1998 | Wang ........................ 73/23.42 |
| 5,792,943 A | * | 8/1998 | Craig ....................... 210/198.2 |
| 5,804,701 A | * | 9/1998 | Berger ....................... 73/23.42 |
| 5,988,703 A | * | 11/1999 | Craig ........................... 219/93 |
| 6,102,068 A | * | 8/2000 | Higdon et al. .............. 137/269 |
| 6,365,105 B1 | * | 4/2002 | Waters et al. ............ 210/198.2 |
| 6,423,120 B1 | * | 7/2002 | Nickerson et al. ....... 210/198.2 |

* cited by examiner

*Primary Examiner*—Edward Lefkowitz
*Assistant Examiner*—Michael Cygan

(57) ABSTRACT

A planar manifold that integrates all the control pneumatics, electronic pressure controls (EPC), and injector inlet onto a single plate, therefore eliminating numerous seals, fittings and transfer tubing between these devices. The planar manifold utilizes plates of specific geometry that minimizes heat transfer between the heated components and the unheated components in the planar manifold, while maintains the mechanical rigidity to support the attached components during shock and vibration. The planar manifold not only improves the reliability and manufacturability of micro gas chromatographs, but also lowers the cost of production.

6 Claims, 5 Drawing Sheets

PLANAR MANIFOLD WITH INTEGRATED HEATED INJECTOR INLET AND UNHEATED PNEUMATICS

FIELD OF INVENTION

The present invention relates generally to miniaturized planar device for liquid and gas phase analysis. More specifically, the invention relates to a planar manifold that integrates heated inlets with unheated pneumatics on the same plate.

BACKGROUND OF THE INVENTION

A gas chromatograph (GC) is an analytical instrument that takes a gaseous sample (or converts a sample to the gaseous state if necessary), and separates the sample into individual compounds, allowing the identification and quantification of those compounds. The principal components of a typical gas chromatograph are the following: an injector that converts sample components into gases (if necessary) and moves a representative sample of the mixture onto the head of a separation column in a narrow band; a separation column that separates the sample mixture into its individual components as these components are swept through the column by an inert carrier gas, the separation being based on differential interactions between the components of the sample mixture and an immobilized liquid or solid material within the column; a detector that detects and measures components as they exit the separation column; and a data display.

Typical modern GC instruments are configured with a heated-block "flash evaporator" type injector, a long capillary tube column, an oven housing the column to maintain and to change the column's temperature in a predictable and reproducible fashion, a flame ionization detector (or other type of detector), and a computer with dedicated hardware/software to process the data collected. Conventional GC units are typically about the size of a large microwave oven (50–100 kg), require 2 to 3 kilowatts of power and considerable air conditioning.

Micro GCs are portable GC systems that are light, rugged and fast. Micro GCs use only utilities (compressed gas and electricity) that are readily available in the field. The micro GCs, smaller than a briefcase, have been widely used not only in field applications, such as custody transfer, well logging, environmental screening, and storage tank analysis, but also in laboratories because micro GCs require minimal laboratory space and operate at high speed with minimal consumption of utilities (compressed gases, air conditioning, etc.).

An important part of a GC system is the accurate control of fluid flow, which is typically achieved with an extensive and complex array of channels, tubing, fittings and the like in a conventional GC. U.S. Pat. No. 5,686,657, herein incorporated by reference, discloses a method to reduce external connections between fluid-handling devices by use of a single planar manifold for the provision of a plurality of flow paths. The fluid-handling devices that connect to the planar manifold are preferably constructed to be surface-mounted, which has been found to offer reliable, fluid-tight connection without the complexity and difficulty of conventional pneumatic connections. The number and complexity of external connections, which would otherwise undesirably increase the volume of the flow system, are also decreased. Another advantage is that the reliability of the pneumatic connections is improved.

A further advantage of the planar manifold technology is that multiple fluid-handling functional devices may be coordinated and assembled in a small volume. Multiple pneumatic channels can be integrated in a planar manifold, which is itself quite compact and amenable to construction in a variety of shapes and configurations. For example, it is contemplated that a planar manifold may be constructed in an irregular shape, such as a curved, bent, or multiple-angled configuration, so as to conform to an irregularly-shaped, compact volume.

A diffusion bonding method is one of the preferred methods to manufacture planar manifolds. In the diffusion bonding method, bonding members to be bonded to each other are held in close contact with each other, and pressed to a degree so that the bonding members are bonded by the diffusion of atoms which takes place in the interface between the bonded surfaces. Since the bonding members are actually "melted" into each other under the bonding conditions, diffusion bonding provides satisfactory bonding strength, air-tightness, and pressure resistance that are required in a pressured fluid-handling system.

Diffusion bonded planar manifolds have been used to perform gas supply functions that relate to injector inlets or detectors in conventional GCs, such as the Agilent 6890 Plus GC system. FIG. 1 shows a block diagram of a prior art GC unit 10. This typical GC unit 10 comprises a computer 12, a controller 14, an injector inlet 16, a detector 18, a column 20, an oven 22, a column heater 28, and a plurality of planar manifolds 24 and 26.

In order to perform a chromatographic separation of a given sample compound, a sample is injected with a pressurized carrier gas by means of the injector inlet 16. The carrier gas supplied to inlet 16 is provided from a source 16A through one or more inlet planar manifold(s) 24, each of which serves in part to control and redirect a plurality of gas flows. The column 20 is positioned within the oven 22 which has an operating temperature of between room temperature and about 450° C. The carrier gas/sample combination passing through column 20 is exposed to a temperature profile resulting in part from the operation of the column heater 28 within oven 22. During this profile of changing temperatures, the sample will separate into its components primarily due to differences in the interaction of each component with the column 20 at a given temperature. As the separated components exit the column 20, the components are detected by the detector 18 which requires a plurality of detector gasses of appropriate types, such as air, hydrogen, and make-up gas. The detector gases are provided from respective sources 18A through one or more detector planar manifold(s) 26. The inlet planar manifolds 24 and detector planar manifolds 26 are placed in a GC manifold carrier 30. Suitable fluid-handling devices, such as fittings, regulators, valves, sensors, and the like in the planar manifolds 24 and 26 may be passive (such as a termination fitting) or active and hence operated under the control of the computer 12 by way of control signals provided the controller 14.

To avoid a "cold spot" or "condensing point", the injector inlet 16 and detector 18 are both heated in their respective heated zones 17 and 19. Since the various valves and electronic pressure controls (EPC) in the planar manifolds 24 and 26 are usually operated at room temperature, the GC manifold carrier 30 is located outside the oven 22 and is connected to the inlet 16 and the detectors 18 by stainless steel tubing 32. Furthermore, all prior art designs use separated planar manifolds for injector inlet and detector gas supplies.

Up until now, micro GCs have not used diffusion bonded planar manifold technology. Instead, micro GCs use discrete stainless steel tubing, machined manifold blocks, o-ring seals, and press fit tapered unions with UV-glue to integrate the gas supply pneumatics and injector device together. Micro-GCs are currently designed to use iso-thermal ovens, and operate over a narrower temperature range of between room temperature to about 120° C.

SUMMARY OF THE INVENTION

Disclosed is a diffusion bonded planar manifold integrating a variety of fluid handling devices that require different operating temperatures onto a single plate. The diffusion bonded planar manifold comprises a high temperature zone for devices requiring high operating temperatures, a low temperature zone for devices requiring lower operating temperatures, and an insulating zone to separate the high temperature zone from the low temperature zone. The insulating zone is designed with such a geometry that heat transfer between the high temperature zone and the low temperature zone is minimized while the mechanical rigidity of the diffusion bonded planar manifold is maintained.

In a preferred embodiment, the high temperature zone is surrounded by a frame which limits heat transfer and provides convection barrier around the devices requiring high operating temperatures.

In another preferred embodiment, the low temperature zone is attached to a heat sink, i.e., a large piece of heat conductive material, that absorbs heat from the low temperature zone and helps to maintain the temperature in the low temperature zone within a desired range.

DETAILED DESCRIPTION OF THE PREFERRED EMBODIMENTS

The diffusion bonded planar manifold will find useful application in a variety of analytical systems containing fluid handling functions operating at different temperatures. Gases are the preferred fluids according to the practice of the present invention, and therefore the following description will include a description of the arrangement, construction, and operation of certain pneumatic devices, and hence is particularly directed to the control of a plurality of gaseous streams in an inlet or detector in a gas chromatographic analytical system. However, for the purposes of the following description, the term "pneumatic" will also be considered to refer to all types of fluids.

Figure 1:
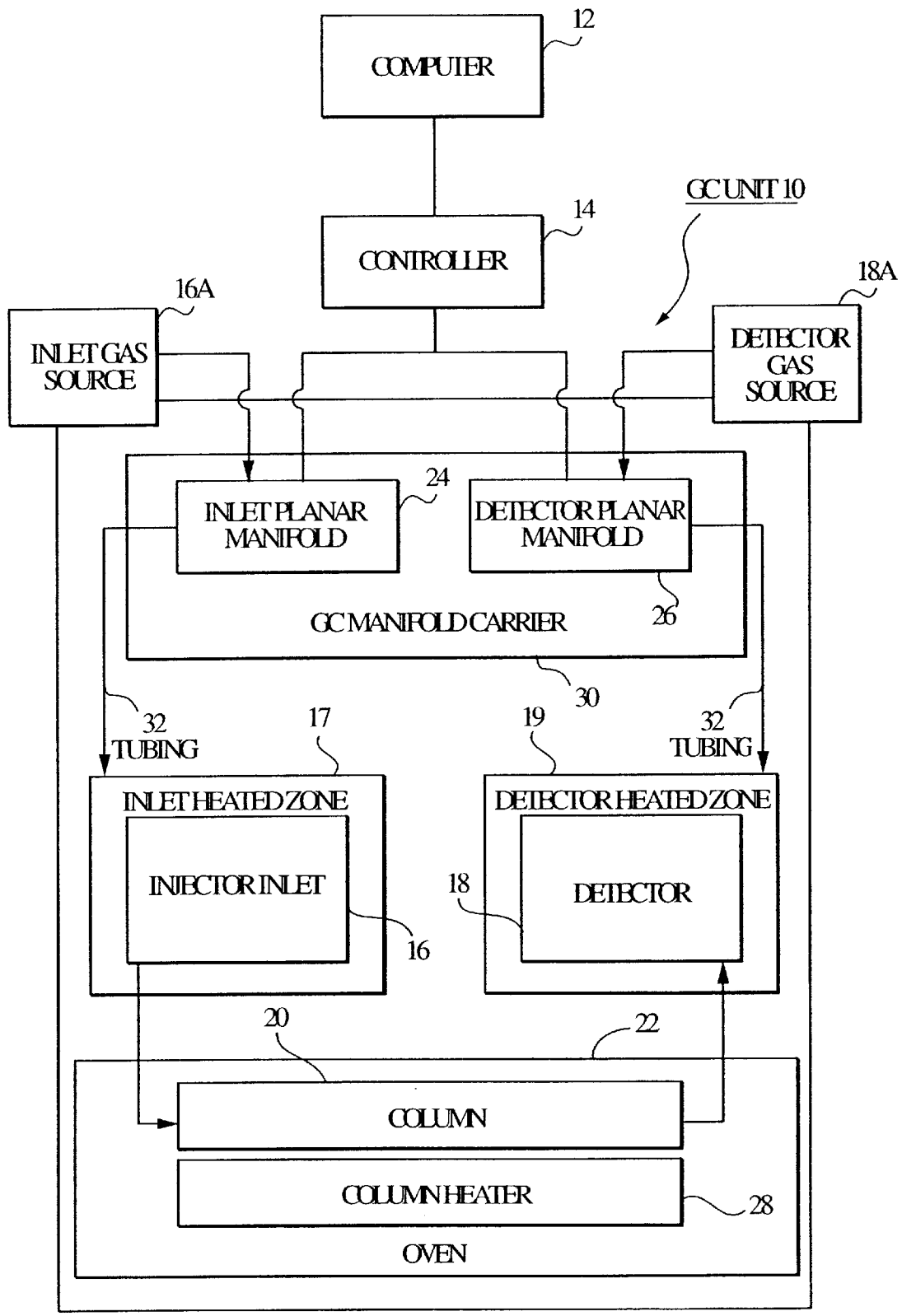
FIG. 1 is a block diagram showing a prior art conventional GC.
Figure 2:
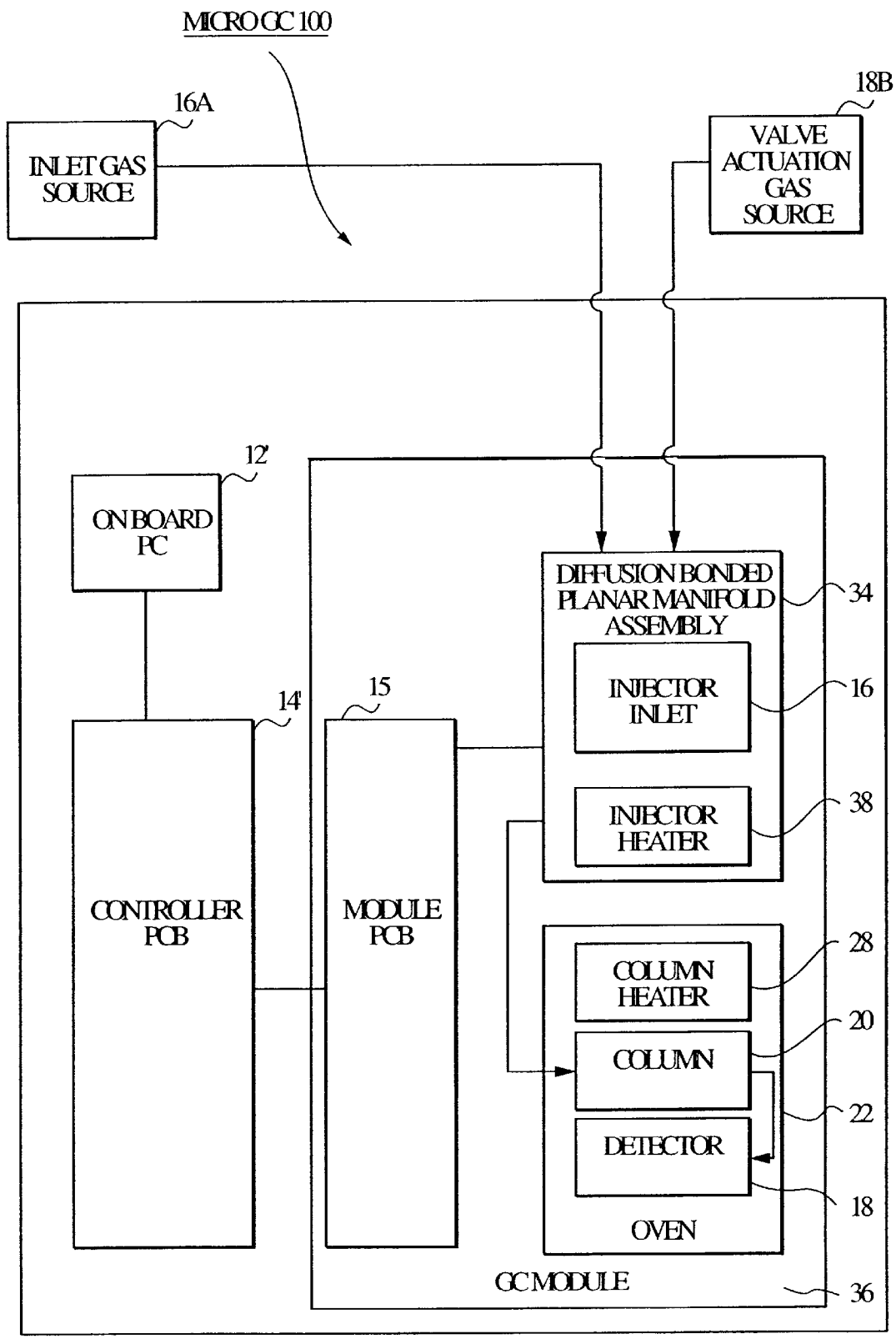
FIG. 2 is a block diagram of an embodiment of the present invention.

FIG. 2 shows a block diagram of an embodiment. This embodiment provides a diffusion bonded planar manifold assembly 34 for a micro GC 100. The micro GC 100 preferably includes an on board computer 12', a controller printed circuit board (PCB) 14', and a GC module 36. The GC module 36 preferably includes a module PCB 15, a diffusion bonded planar manifold assembly 34, a detector 18, a column 20, an oven 22 and a column heater 28. The diffusion bonded planar manifold assembly 34 preferably combines all the control pneumatics (not shown in FIG. 2), EPC (not shown in FIG. 2), an injector inlet 16 and an injector heater 38 into a single assembly, hence eliminating numerous seals and transfer tubing and improving the reliability and manufacturability of the micro GC 100. Two gas sources 16A and 18B are provided. The inlet gas source 16A provides one or more gases for the column 20. The gas flow is divided by an injector die (not shown) within the diffusion bonded planar manifold assembly 34 into analytic and reference flows for the needs of the detector. The valve actuation gas source 18B provides one or more gases to actuate pilot valves. An alternative might be to provide a single supply of gas to be divided by the diffusion bonded planar manifold into an appropriate number of gas streams. This embodiment incorporates the existing planar manifold uses of gas regulation with the new uses in the heated injector and sample stream realm.

Figure 3:
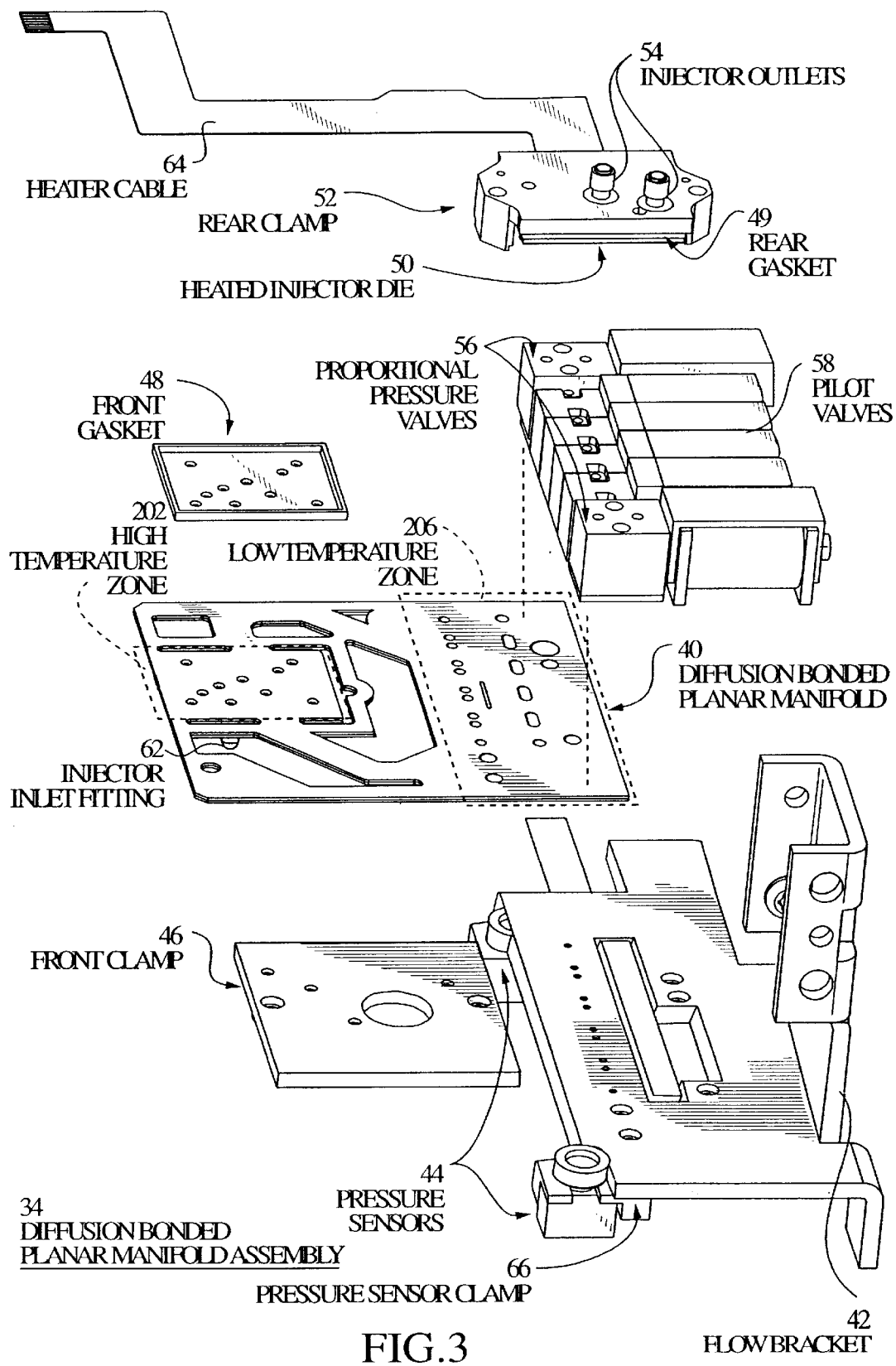
FIG. 3 is a exploded view of a preferred embodiment of a diffusion bonded planar manifold assembly.

FIG. 3 depicts an exploded view of a preferred embodiment of a diffusion bonded planar manifold assembly 34 in the micro GC 100 of FIG. 2. The diffusion bonded planar manifold assembly 34 preferably comprises a flow bracket 42, one or more pressure sensors 44, one or more pressure sensor clamps 66, a front clamp 46, a front gaskets 48 and a rear gasket 49, a heated micro electronic machine system (MEMS) injector die 50 with injector outlets 54, a heater cable 64, a rear clamp 52, one or more proportional pressure valves 56, and a plurality of pilot valves 58, and a diffusion bonded planar manifold 40 with an injector inlet fitting 62 and a plurality of manifold ports (not shown) for the attachment of the pressure sensors 44, the MEMS injector die 50, and the valves 56 and 58.

Devices and components held between the front clamp 46 and the rear clamp 52 constitute a high temperature zone 202 on the left part of the diffusion bonded planar manifold 40 (i.e., the area for the attachment of the heated injector die 50), where the sample temperature is typically controlled to several degrees under an oven setpoint. Devices and components attached on the right part of the diffusion bonded planar manifold 40 constitute a low temperature zone 206 (i.e., the area for the attachment of the pilot valves 58 and the proportional pressure valves 56), where the temperature is usually near ambient.

Figure 4:
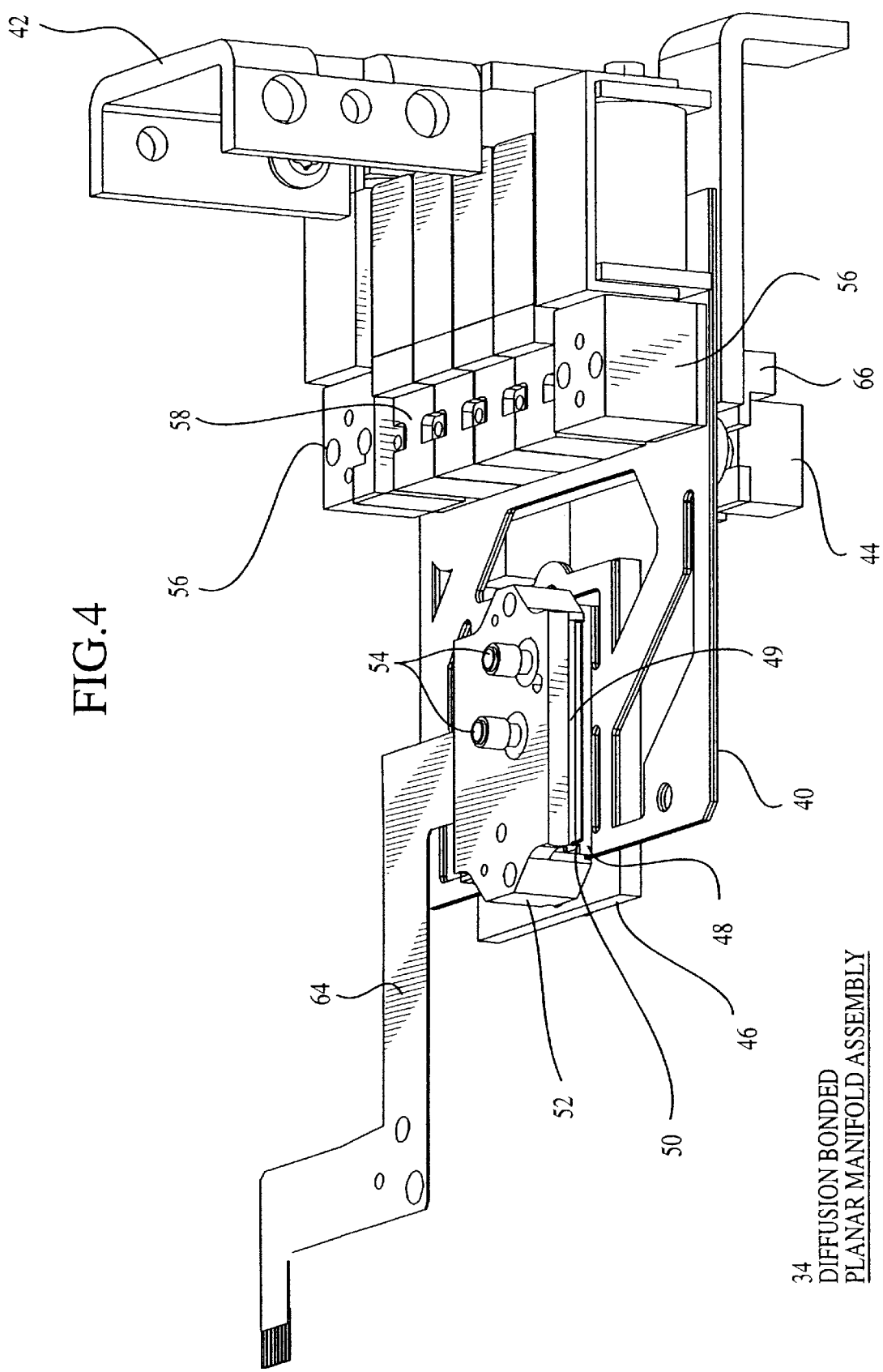
FIG. 4 is a side perspective view of an assembled diffusion bonded planar manifold assembly of FIG. 3.

FIG. 4 illustrates an assembled diffusion bonded planar manifold assembly 34. The two pressure sensors 44 are preferably mounted to the flow bracket 42 through the pressure sensor clamps 66. The diffusion bonded planar manifold 40 is preferably made of stainless steel and mounted to the flow bracket 42 on top of the pressure sensors 44. The proportional valves 56 and the pilot valves 58 are preferably mounted on the opposite side of the diffusion bonded planar manifold 40 from the pressure sensor clamps 66. The heated injector die 50 is preferably sandwiched between the front gasket 48 and the rear gasket 49, and is preferably mounted to the diffusion bonded planar manifold 40 on the opposite side of the injector inlet fitting 62. A heater (not shown) is located between the rear gasket 48 and the injector die 50. The diffusion bonded planar manifold 40, the heated MEMS injector die 50, the heater, and the two gaskets 48 are preferably clamped together by the front clamp 46 and the rear clamp 52. The precise alignment between the diffusion bonded planar manifold 40 and the attached fluid-handling devices are provided by a plurality of register pins and dowels (not shown). A number of O-rings (not shown in FIG. 4) built into the gasket create seals between the surface mounted fluid-handling devices and the diffusion bonded planar manifold 40.

Figure 5:
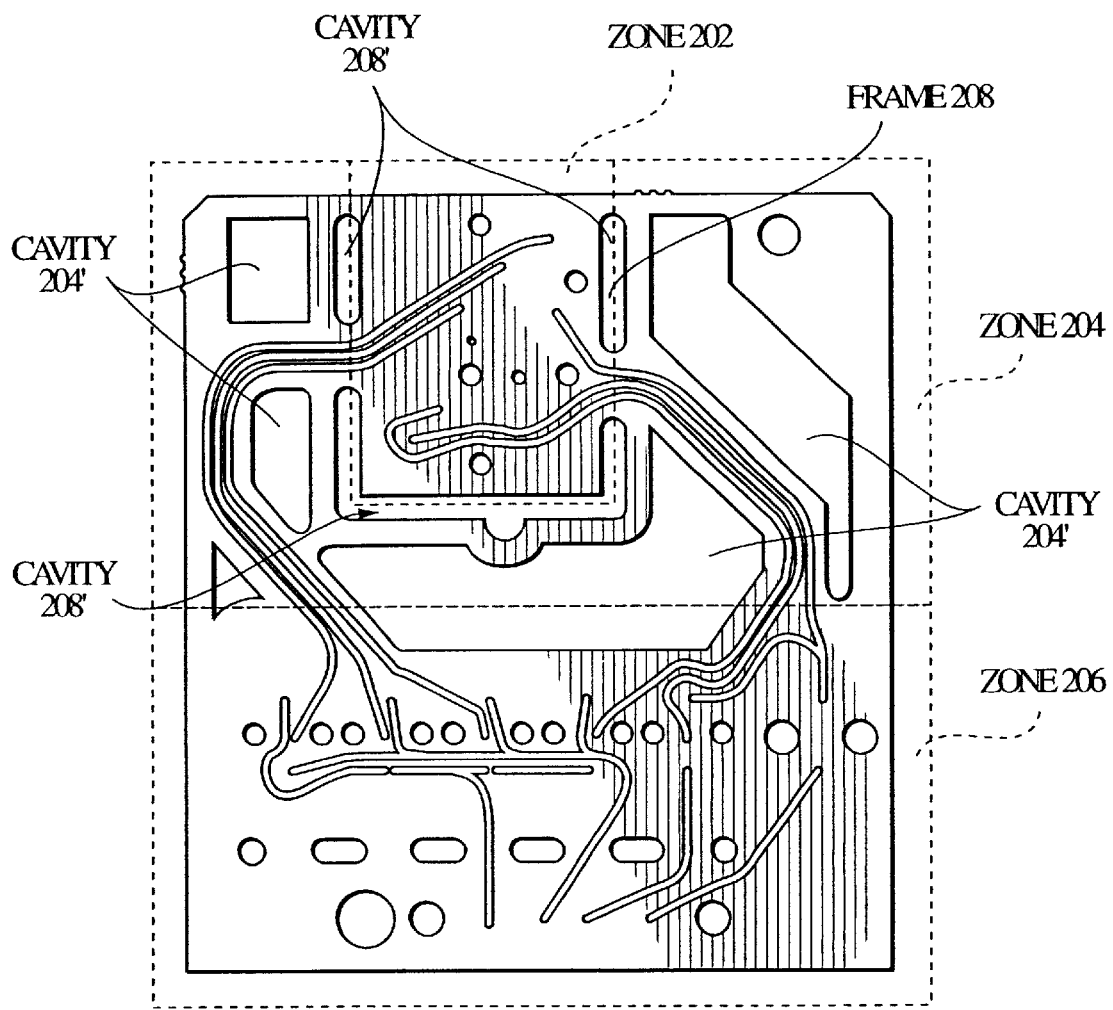
FIG. 5 is an inside view of the diffusion bonded planar manifold of FIG. 3.

FIG. 5 shows a detailed view of the diffusion bonded planar manifold 40 of FIG. 3 and FIG. 4. Based on the required operating temperature of the attached devices, the diffusion bonded planar manifold 40 is preferably divided into three zones: the high temperature zone 202, the low temperature zone 206, and a insulating zone 204 between the high temperature zone 202 and the low temperature zone 206. The high temperature zone 202 preferably matches the geometry of the MEMS injector die 50, and is uniformly heated to about 120°. The low temperature zone 206 preferably matches the required valve footprints for the proportional pressure valves 56 and the pilot valves 58, which have a maximum operating temperature of 40°–60°.

To limit heat transfer out of the high temperature zone 202 to ambient or to the low temperature zone 206, the high temperature zone 202 is preferably insulated in the front (i.e., the side facing the front clamp 46) and on the back (i.e., the side facing the rear clamp 52). In addition, the high temperature zone 202 is preferably surrounded by a frame 208 which limits heat transfer and provides a convection barrier around edges of the high temperature zone 202. The frame 208 preferably defines one or more cavities 208' that surround the high temperature zone 202.

The heat transfer through the diffusion bonded planar manifold 40 is further minimized by the insulating zone 204. The insulating zone 204 is designed to connect the high temperature zone 202 to the low temperature zone 206 with minimal material in order to limit heat transfer, while still providing a conduit for fluid flows and enough mechanical rigidity to support the MEMS injector die 50 during shock and vibration. The insulating zone 204 preferably defines one or more cavities 204' that reduce heat transfer through the diffusion bonded planar manifold 40. In addition, the low temperature zone 206 is preferably mounted on the flow bracket 42 that functions as a "heat sink" to absorb the excess heat from the low temperature zone 206. The flow bracket 42 is preferably made of a heat conductive material, preferably aluminum.

While the invention has been described and illustrated with reference to specific embodiments, those skilled in the art will recognize that modification and variations may be made without departing from the principles of the invention as described herein above and set forth in the following claims.

What is claimed is:

1. A planar manifold with a plurality of pneumatic channels therein, comprising:
   a high temperature zone comprising manifold ports for the attachment of fluid-handling devices, the high temperature zone having cavities through the planar manifold opening onto the major surfaces thereof at the perimeter of the high temperature zone;
   a low temperature zone comprising manifold ports for the attachment of unheated fluid-handling devices; and
   an insulating zone thermally separating the high temperature zone from the low temperature zone, the insulating zone including cavities through the planar manifold opening onto the major surfaces thereof, such cavities on the major surfaces in the insulating zone being larger in area than the cavities on the major surfaces at the perimeter of the high temperature zone and being located a further distance from the high temperature zone than the cavities at the perimeter thereof, the cavities in the insulating zone and the cavities at the perimeter of the high temperature zone being shaped and being spaced apart such that they define a frame around the perimeter of the high temperature zone and a path connecting the high temperature zone and the insulating zone, pneumatic channels extending across the insulating zone and across the path into the high temperature zone to communicate with manifold ports therein, the frame limiting the heat transfer from the high temperature zone to the insulating zone.

2. The planar manifold of claim 1 wherein the path connecting the high temperature and insulation zones is at the mid-region of one of the sides of the high temperature zone.

3. The planar manifold of claim 2 wherein the cavities at the perimeter of the high temperature zone are elongated.

4. The planar manifold of claim 3 wherein the laterally extending portion at each end of first elongated portion extends normal thereto.

5. A planar manifold assembly comprising:
   a planar manifold with a plurality of pneumatic channels therein, the planar manifold having a high temperature zone that comprises manifold ports for the attachment fluid-handling devices, the high temperature zone having cavities through the planar manifold opening on the major surfaces thereof at the perimeter of the high temperature zone, a low temperature zone that comprises manifold ports for the attachment fluid-handling devices, an insulating zone that thermally separates the high temperature zone from the low temperature zone, the insulating zone including cavities through the planar manifold opening on the major surfaces thereof, such cavities on the major surfaces in the insulating zone being larger in area than the cavities on the major surfaces at the perimeter of the high temperature zone such cavities and being located at a distance further from the high temperature zone than the cavities at the perimeter, the cavities in the insulating zone and the cavities at the perimeter of the high temperature zone being shaped and being spaced apart such that they define a frame around the perimeter of the high temperature zone and a path connecting the high temperature zone and the insulating zone, pneumatic channels extending across the insulating zone and across the path into the high temperature zone to communicate with manifold ports therein, such frame limiting the heat transfer from the high temperature zone to the low temperature zone; and
   a heat source in conductive heat transfer relation with the high temperature zone of the planar manifold.

6. The planar manifold assembly of claim 5 wherein the heat source is a heated injector die in conductive heat transfer relation with the high temperature zone of the planar manifold.

* * * * *